US005487889A

United States Patent [19]
Eckert et al.

[11] Patent Number: 5,487,889
[45] Date of Patent: Jan. 30, 1996

[54] BANDAGE FOR CONTINUOUS APPLICATION OF BIOLOGICALS

[75] Inventors: Richard L. Eckert, Cleveland Heights; Daniel J. Smith, Stow; Irwin Schafer, Brutenahl, all of Ohio

[73] Assignees: The MetroHealth System; The University of Akron; Case Western Reserve University, both of Cleveland, Ohio

[21] Appl. No.: 106,165

[22] Filed: Aug. 13, 1993

Related U.S. Application Data

[63] Continuation-in-part of Ser. No. 893,164, Jun. 3, 1992, abandoned.

[51] Int. Cl.$^6$ .......................... A61F 13/00; C12N 15/00; A61K 38/18
[52] U.S. Cl. ................................ 424/93.1; 514/2; 514/12; 604/304; 604/305; 604/307; 424/93.2; 424/93.21; 424/93.7
[58] Field of Search ........................ 514/2, 12; 604/305, 604/307, 304; 424/443, 445, 446, 447, 93.1, 93.2, 93.21, 93.7; 602/41; 435/240.1, 320.1

[56] References Cited

U.S. PATENT DOCUMENTS

| | | | |
|---|---|---|---|
| 4,185,095 | 1/1980 | Young | 424/177 |
| 4,287,184 | 9/1981 | Young | 424/177 |
| 4,444,760 | 4/1984 | Thomas, Jr. | 424/177 |
| 4,563,184 | 1/1986 | Korol | 604/368 |
| 4,621,052 | 11/1986 | Sugimoto | 435/69.1 |
| 4,661,455 | 4/1987 | Hubbard | 435/240 |
| 4,708,948 | 11/1987 | Iwata et al. | 514/2 |
| 4,721,672 | 1/1988 | Valee et al. | 435/70.1 |
| 4,743,679 | 5/1988 | Cohen et al. | 530/350 |
| 4,747,845 | 5/1988 | Korol | 604/368 |
| 4,762,124 | 8/1988 | Kerch et al. | 604/307 |
| 4,816,561 | 3/1989 | Todaro | 530/324 |
| 4,857,334 | 8/1989 | Korol et al. | 424/445 |
| 4,861,757 | 8/1989 | Antoniades et al. | 514/21 |
| 4,874,746 | 10/1989 | Antoniades et al. | 514/21 |
| 4,876,242 | 10/1989 | Applebaum et al. | 514/3 |
| 4,882,275 | 11/1989 | Klagsbrun | 435/69.1 |
| 4,885,163 | 12/1989 | Shaar et al. | 514/2 |
| 4,944,948 | 7/1990 | Uster et al. | 424/450 |
| 4,959,353 | 9/1990 | Brown et al. | 514/12 |
| 4,966,849 | 10/1990 | Valee et al. | 435/199 |
| 4,981,841 | 1/1991 | Gibson | 514/2 |
| 4,983,580 | 1/1991 | Gibson | 514/2 |
| 4,983,581 | 1/1991 | Antoniades et al. | 514/12 |
| 5,092,323 | 3/1992 | Reidel et al. | 602/54 |
| 5,096,825 | 3/1992 | Barr et al. | 435/255.1 |
| 5,147,339 | 9/1992 | Sundstrom | 604/307 |
| 5,152,757 | 10/1992 | Eriksson | 604/305 |
| 5,167,613 | 12/1992 | Karami et al. | 602/42 |
| 5,182,111 | 1/1993 | Aebischer et al. | 424/424 |
| 5,423,778 | 6/1995 | Eriksson et al. | 604/305 |

OTHER PUBLICATIONS

Sanders, P. G. et al., *Animal Cell Biotechnology*, 4:17–70, 1990.

"Tumorigenic Keratinocyte Lines Requiring Anchorage and Fibroblast Support Cultured from Human Squamous Cell Carcinomas," by J. G. Rheinwald et al., *Cancer Research*, May 1981, pp. 1657–1663.

"Stable Expression of Transfected Human Involucrin Gene in Various Cell Types: Evidence for In Situ Cross–Linking by Type I and Type II Transglutaminase," by E. A. Rorke et al., *The Journal of Investigative Dermatology*, Feb. 26, 1991, pp. 543–548.

"Replacement of Insulin Receptor Tyrosine Residues 1162 and 1163 Compromises Insulin–Stimulated Kinase Activity and Uptake of 2–Deoxyglucose," by L. Ellis et al., Hormone Research Inst., San Francisco, Calif., Feb. 18, 1986, pp. 721–732.

"Construction of a Novel Oncogene Based on Synthetic Sequences Encoding Epidermal Growth Factor," D. Stern et al., Jan. 16, 1987, pp. 321–324.

Abstracts: "Growth Hormone is an Oncogenic Growth Stimulator When Expressed in Human Epidermal Keratinocytes," S. Andreatta–VanLeyen et al., *Journal of Invest. Dermatology*, vol. 98, No. 4, Apr. 1992.

"Alternative Processing of Bovine Growth Hormone mRNA: Nonsplicing of the Final Intron Predicts a High Molecular Weight Variant of Bovine Growth Hormone," by R. Hampson et al., *Proc. Natl. Aca. Sci. USA*, vol. 84, pp. 2673–2677, May 1987.

"Human Growth Hormone in the Blood of Athymic Mice Grafted With Cultures of Hormone–Secreting Human Keratinocytes," by J. Teumer et al., *The FASEB Journal*, vol. 4, pp. 3245–3250, Nov. 1990.

"Immortalization of Human Keratinocytes by Simian Virus 40 Large T–Antigen Alters Keratin Gene Response to Retinoids," by Chapla Agarwal et al., *Cancer Research*, vol. 50, pp. 5947–5953, Sep. 15, 1990.

*Primary Examiner*—Marianne P. Allen
*Attorney, Agent, or Firm*—Calfee Halter & Griswold

[57] ABSTRACT

The present invention provides a biological bandage, comprising an envelope enclosing cells which secrete biologically active cellular products such as growth factors, which promote the healing of wounds. The envelope is further comprised of a permeable bottom membrane through which the cellular product diffuses, and a top membrane. Preferably the bandage has a separator interposed between the two membranes. This invention also relates to a method for treating wounds. The bandage provides a continuous, uniform source of fresh cellular product.

31 Claims, 9 Drawing Sheets

BANDAGE FOR CONTINUOUS APPLICATION OF BIOLOGICALS

CROSS REFERENCE TO RELATED APPLICATIONS

This application is a continuatation-in-part of U.S. application Ser. No. 07/893,164, filed Jun. 3, 1992 now abandoned.

FIELD OF THE INVENTION

This invention relates to a bandage which continuously provides curative cell products to a wound. More particularly, the invention relates to: a bandage having a chamber for containing cells and cell culture media, said bandage having a cell product permeable membrane; to genetically engineered cells useful in said bandage; and to a method for producing such cells.

BACKGROUND OF THE INVENTION

The treatment of wounds in mammals, both animals and humans, has historically involved a simple passive bandage which provides physical protection and, to some extent, reduces infection. The treatment has progressed from this simple bandage to more active treatments. In serious wounds, particularly burns, skin grafting and skin sheets have been applied. Eventually the skin cells "take" and fill in the wound.

Attempts have been made to expedite healing by introduction of various growth factors directly into the wound, see Brown G. L., Curtsinger L., Jurkiewicz M. J., Nahi F., Schultz G., (1991) "Stimulation of Healing of Wounds by Epidermal Growth Factor," Plast. Reconstr. Surg , Vol. 88, pp. 189–194; Brown G. L., Nanney L. B., Griffen J., Cramer A. B., Yancey J. M., Curtsinger L., Holtzin L., Schultz G., Jurkiewicz M. J., and Lynch J. B. (1989).

"Enhancement of Wound Healing by Topical Treatment with Epidermal Growth Factor," New England J. Med., Vol. 321, pp. 76–79; ten Dijke P., Iwata K. K., "Growth Factors for Wound Healing" (1989) Biotechnology, Vol. 7, pp. 793–798; Pierce G. F., Mustoe T. A., Altrock B. W. Deuel T. F., Thomason A., (1991), "The Role of Platelet Derived Growth Factor in Wound Healing Cellular Biochemistry," Vol. 45, pp. 319–316; and, "EGF and PDGF-Alpha in Wound Healing and Repair," Schultz Rotatori and Clark, J. of Cellular Biochemistry, Volume 45, pp. 346–352 (1991).

Growth factors encourage the proliferation and/or differentiation of the cells in the tissue within and around the wound. Several attempts have been made to introduce these growth factors into the wound by means of a topical gel or the like, applied over the surface of the wound. However, such growth factor containing gels have several drawbacks. The amount of growth factor contained in these gels is fixed. Over time, the enzymes produced from the patient's own tissue may degrade the gel and/or the growth factor. Further, the isolation and purification of the growth factor may decrease its biological activity.

Attempts nave been made to drip the growth factor directly into the wound. However, this method of application is not continuous and does not provide a uniform amount of arowth factor to the different areas of the wound.

In addition, many growth factors have a short half life, thus the amount of growth factor delivered to the wound substantially decreases with time. Finally, the cost of the isolated, purified growth factors is extremely high.

While the addition of growth factors to wounds has accelerated wound healing, the above drawbacks have prevented widescale use of the growth factors in wound treatment.

Thus, it would be desirable to have a bandage that could continually supply biologically active growth factors in uniform amounts directly to wounded tissue.

SUMMARY OF THE INVENTION

The bandage of this invention generally comprises an envelope defined by an upper membrane and a lower membrane which is permeable to a biological such as a growth factor or a hormone, derived from cells maintained in a nutrient media present within said envelope. The biological is preferably a growth factor or growth hormone. A separator is optionally positioned between the upper and lower membranes.

The invention provides methods for making such a bandage and for the treatment of wounds by the application thereof.

Another aspect of the invention provides genetically engineered genes which produce various growth factors, methods for the production of such genes, cells transformed therewith, and the products, including expression products, of such cells.

DETAILED DESCRIPTION OF THE DRAWINGS

DETAILED DESCRIPTION OF THE INVENTION

The present invention provides a novel bandage for applying fresh biologically active molecules, such as growth factors, or growth hormones directly to a wound, in a time released, continuous uniform manner.

Figure 1:
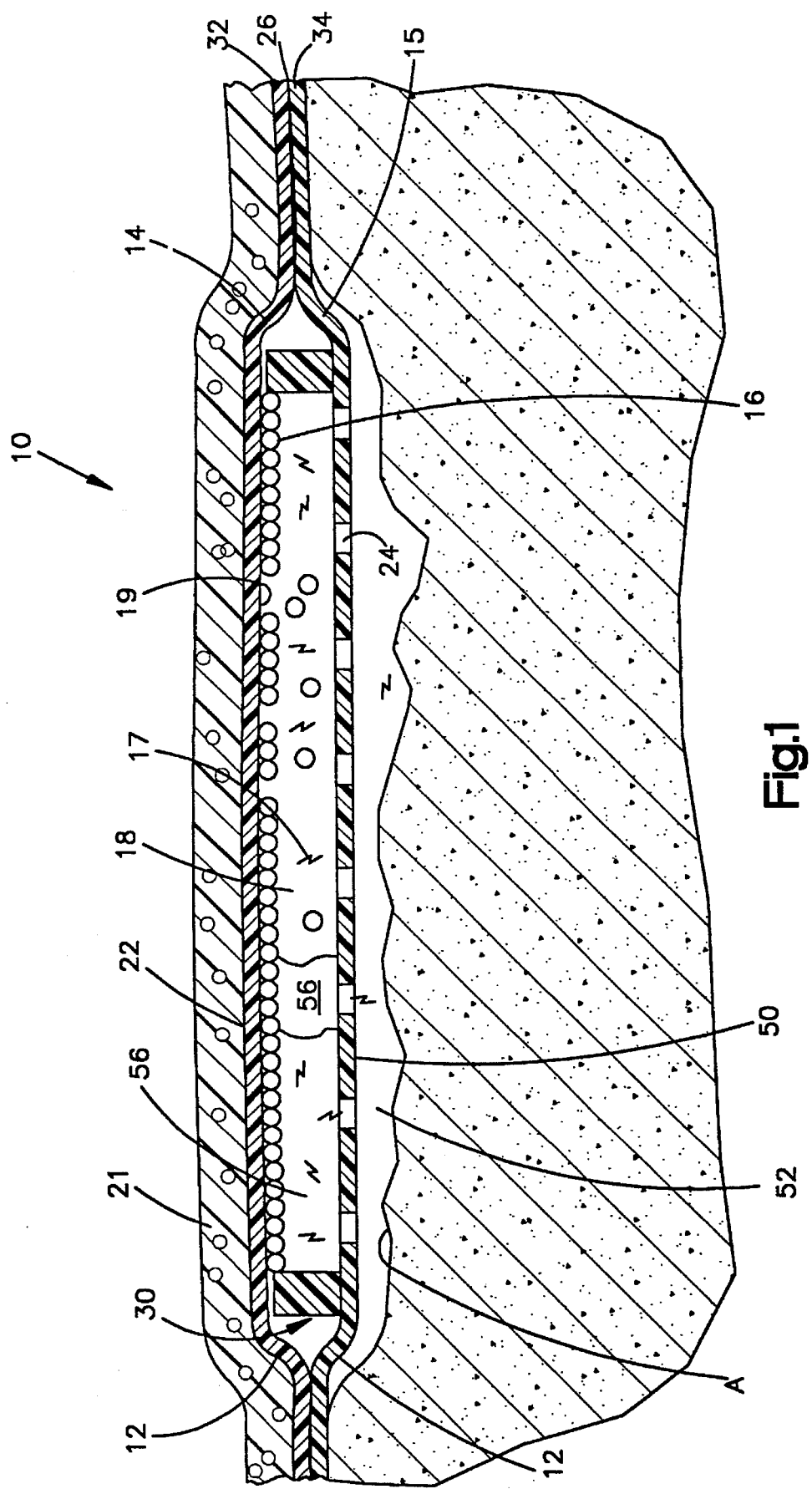
FIG. 1 is a cross-sectional view of the enclosed separator embodiment of the bandage.

As shown by FIG. 1, the bandage 10 comprises: an envelope 12, having a top membrane 14, a bottom membrane 15; a chamber 56; cells 16 which produce the cellular product 17; and cell nutrient medium 18 contained in said chamber 56. The fresh biologically active cellular product 17 diffuses through the bottom membrane 15 and into the wound. Since the cells 16 continue to produce the cellular product, the wound receives it in a continuous manner. The bandage 10 can increase the rate of wound healing in mammals, including humans.

USE OF THE BANDAGE

The rate of wound healing is improved with only a single growth factor provided by a single bandage. Thus, treatment solely with platelet derived growth factor (PDGF), transforming growth factor (TGF), or epidermal growth factor (EGF), will increase the rate of wound healing. However, combining the use of various growth factors, preferably in sequence, in the treatment of the wound will further increase the rate of healing.

Preferably, the wound is treated with, for example, three different growth factors produced from three different cell types, in three different bandages. For example, it is preferred that the first bandage contain cells producing PDGF, which would trigger an immune response thereby promoting macrophage invasion and angiogenesis. Thereafter, in approximately 2–3 days, the first bandage would be removed and a second bandage containing cells which produce TGF-beta would be applied. TGF-beta causes the patient's own fibroblasts, the cells that comprise the tissue matrix below the skin, to proliferate and/or differentiate thereby increasing the collagen fiber production in the wound area. After approximately 2–3 days the second bandage would be removed and a third bandage containing cells which produce the epidermal growth factor, would be applied. The epidermal growth factor would increase the growth of the patient's epidermal cells and close the wound.

Alternatively, a single bandage could be used, in which one type of cell is removed from and another type of cell injected into the bandage by a syringe or which is constructed to release multiple cell products such as growth factors, simultaneously.

The bandage of the invention is used on a variety of wounds such as, for example, pressure sores, burns, abrasions and evendeeper wounds. In addition, the bandage is used to treat skin conditions such as psoriasis. Also the bandage is used to accelerate the healing of skin grafts and to enhance the "take" of cultured keratinocytes which have been placed into the wound.

The bandage is also be used to provide a delivery system for cellular products to an organism.

THE ENVELOPE

The envelope or outer portion of the bandage surrounds and encloses the cells 16 and nutrient medium 18. The size of the envelope, which determines the size of the bandage, is determined by the size of the wound. While the envelope may optionally be made of a single piece of material, preferably the envelope is comprised of separate top and bottom membranes 14 and 15.

TOP MEMBRANE

The top membrane 14 is preferably made of a gas permeable, preferably hydrophilic, material which preferably bars the entry of organisms such as viruses and bacteria into the bandage. The top membrane should be permeable to gases such as oxygen and carbon dioxide, and have a thickness of from about 0.5 mils to about 20 mils, preferably about 6 mils. Preferably the top membrane 14 is comprised of a modified hydrophilic polysulfone, available under the trade name Z-Bind®, from Gelman Sciences, Inc. which has a pore size of about 0.2–0.4 micrometers.

A variety of polymeric materials are used for the top membrane, such as, for example, polypropylene or polyethylene which are impermeable to fluids and do not elicit an immune response or inflammation.

The top membrane alternatively may be comprised of materials of the type available under the trade name "Celgard 5550" from the Hoechst Celanese Company. Celgard 5550 is comprised of a uniform non-woven polypropylene fiber web and Celgard 2500, a polyethylene film. The Celgard 5550 has a pore size of 0.075×0.25 microns in diameter with 45% porosity and a moisture transmission rate of 460 g/m$^2$/24 hours. Alternatively, "Metricel®polypropylene," a hydrophobic membrane having a 0.1 micron pore size, available from Gelman Science, Inc., Ann Arbor, Mich., is suitable. Also, suitable materials for the top membrane include those materials identified below as suitable for the bottom membrane 15.

The thickness of the top membrane must be sufficient to contain the contents of the bandage and yet be flexible to permit patient movement. A thickness from about 3 mils to 7 mils is typically sufficient. The Celgard 5550 is about 3 mils, the Celgard 2500 being about 1 mil.

Where the cells 16 are anchorage dependent cells, such as 'SCC-13' cells, they require a surface to grow on. Typically this surface will be either the inner surface 19 of top membrane 14 or the inner surface 20 of bottom membrane 15. It is also possible for the cells to grow on both membranes 14 and 15. Where the cells 16 are to grow on the inner surface 19 of the top membrane 14 of a hydrophobic material such as Celgard, the surface is preferably plasma treated. The plasma treatment, such as oxygen or ammonia plasma treatment, provides hydrophilic groups such as amino groups and hydroxyl groups on the inner surface. The presence of such groups facilitates the attachment of the cells to the surface. Plasma treatment is performed by BeCton Dickinson Research Center, Research Triangle Park, North Carolina, a division of Becton Dickinson and Company. The plasma treatment is as specified by Hoechst Celanese, the manufacturer of Celgard. Where the Metricel® polypropylene is used, a similar plasma treatment would be required to enable anchorage dependent cells to grow on the membrane.

Alternatively, the top membrane 14 comprised of a hydrophobic film with a hydrophilic film attached to the inner surface thereof. Such an arrangement provides the required hydrophobicity, while presenting a hydrophilic surface to which the cells may attach.

It is preferred that a layer of foam 21 be attached to the outer surface 22 of the top membrane 14 to provide rigidity to the bandage 10. The foam is of conventional materials, such as a closed cell polyurethane film-laminate, available from Semix Life Sciences Co., Frasier, Penn. preferably applied with an adhesive such as, for example, "Med 1118TT" from Avery Specialty Tape Co., Painsville, Ohio; or a tan spunlaced polyester film available under the trade name "5322P" from Avery Co. Preferably, the foam 21 is flesh colored for aesthetic purposes.

BOTTOM MEMBRANE

The bottom membrane 15 must be permeable to the desired cellular product 17, such as the growth factor or hormone. Preferably, the bottom membrane 15 is not permeable to viruses, bacteria, etc. which could infect the cell culture. While a variety of materials can be used for the bottom membrane 15, polyethylene, available under the trade name "Celgard 5550" from Celanese, is preferred. Celgard is preferred in embodiments where the top membrane 14 is also made of Celgard 5550 and further where the perimeters of top membrane 14 and bottom membrane 15 are fused to form the envelope 12. When used as the bottom membrane the Celgard 5550 is rendered permeable by the manufacturer by a special treatment with a surfactant such as "Tween 80" or "Tween 20" to "wet" at least the pores 24 thereof. Presence of excess surfactant in the pores 24 of the membrane 15 may kill some cells in the chamber 56. To remove excess surfactant the bottom membrane 15 is soaked in 100% ethanol for about 12 hours followed by heating in deionized water for about 10 minutes at 90° C.

The pore size of the bottom membrane 15 must be sufficient to permit diffusion of the cellular product 17 to diffuse through the bottom membrane 15, but still small enough to prevent the passage of larger objects such as bacteria. Where the cellular product 17 is bovine growth hormone, the pore must pass molecules of about 22,000 daltons. Where the cellular product is epidermal growth factor, the membrane should pass molecules of about 6,000 daltons. The typical protein retention for Celgard 5550 membrane is 29% for albumin (mw 67,000), 40% for gamma globulin (mw 160,000) and 98% for fibrinogen (mw 340,000). Typically, the desired cellular product, such as a growth factor, has a molecular weight of less than 30,000 and will not be retained in the pores of the Cellgard 5550 membrane.

Preferably the bottom membrane 15 is comprised of a modified hydrophilic polysulfone, available under the trade name Z-Bind®, from Gelmen Sciences, Inc. which has a pore size of about 0.2–0.4 micrometers and which permits the diffusion of the cellular product 17. Another hydrophilic polysulfone membrane is available under the trade name "UltraSep" from Micron Separations Inc. Another suitable product is available under the trade name "Supor" from Gelmen Sciences, Inc. Supor has a pore size of from about 0.1 to 0.8 microns. Supor is also hydrophilic and permits the diffusion of the cellular product. Alternatively, the bottom membrane is comprised of a polyfluorinated polyethylene (Teflon®) membrane which is surface modified with extracellular matrix protein, available under the trade name "Millicell" from Pharmacia Millipore.

Alternatively, the bottom membrane is comprised of hydrophobic membranes including, for example, Metricel® available from Gelmen Sciences, Inc.; a polycarbonate membrane such as, for example, "MicroClear" from Micron Separation, Inc.; or polyvinyl chloride membranes such as, for example, "Polypure PVC" from Micron Separations, Inc. The MicroClear has a pore size of from about 0.1μ to about 0.8μ and the Polypure has a pore size of about 0.8 microns. Additional hydrophilic membranes include, for example, acrylate copolymer on non-woven nylon, available under the trade name "Versapor" from Gelman Sciences Company and cellulose acetate such as, for example, membranes available under the trade name "Acetate Plus" from Micron Separations, Inc. The Versapor has a pore size of about 0.02 to 3μ and the Acetate Plus has a pore size of about 0.22μ to 0.8μ. Hydrophobic membranes must first be rendered hydrophilic to permit the cellular product to pass through the pores of the membrane. This is accomplished by the plasma treatment under a vacuum, to line the pores with hydrophilic groups, or by treating the membrane with a wound dressing such as Hypol.

Other suitable membranes include glass matrix membranes, available from Gelman Sciences, Ann Arbor, Mich., Millipore, Mass., and Anotec, United Kingdom.

The thickness of the bottom membrane 15 must be sufficient to contain the contents of the bandage yet thin enough to permit the diffusion of the cellular product 17. Typically, the thickness of the bottom membrane ranges from 0.5 mils to 8 mils. The bottom membrane is optionally reinforced with various materials including, for example, nylon webbing. Such reinforcement supports thin bottom membranes and renders it less fragile.

Optional Features

Optionally, although preferably, a hydrophilic, commercially available gel wound dressing 60 such as a hydrocolloid film available under the trade name "Duoderm," from the Convatec Company or a hydrophilic hydrogel available under the trade name "Hypol Hydrogel" from the biodegradable 2000, or 3000 series-a polyurethane prepolymers, from W.R. Grace and Company, is applied to the bottom surface 50 of the bottom membrane 15. Prior to applying the bandage to the wound, the Hypol Hydrogel is reacted with water to provide a gel. When the bandage is applied to the wound, the film absorbs the wound extrudate, thereby hydrating the film to provide a gel 60. The gel serves several functions: to provide a physical cushion between the wound A and the bandage 10; to hydrate the wound; to help prevent wound extrudate from plugging the pores 24 of the bottom membrane 15; and to render hydrophobic bottom membranes hydrophilic. The cellular product 17 satisfactorily diffuses through the gel 60 to reach the wound.

The wound dressing is available as, for example, an adhesive backed film, such as Hydrogel biocompatible adhesive wound dressing form Nepera Inc., Harriman, N.Y. which is applied directly to the bottom surface 50 of the bottom membrane 15. Another suitable wound dressing, Hypol Hydrogel, is dissolved in a 10% solution of toluene and the bottom membrane 15, such as Celgard 2500 is immersed in the solution. Once the bottom membrane 15 is saturated, which occurs in approximately ten seconds, it is removed and dried. Water is then applied to react with the Hypol Hydrogel present within the pores and on the surface of bottom membrane 15 to form a colorless hydrogel. The bottom membrane 15 is thereby rendered hydrophilic to allow the cellular product 17 to pass through the bottom membrane.

Other suitable hydrogels include, for example, "Vigilion," available from Bard Home Health Division, "Intrasite Gel," available from Smith and Nephew Company, "Geliperm," available from Fougera Company, and hydrogel available form Lectech in Minnetonka, Minn. Suitable colloids include, for example, "DuoDerm" available from , ConvaTec, "Restore," available from Hollister, and "Comfeel," available from Kendall. Other hydrogel or hydrocolloid films; which achieve the above-described purpose are also suitable.

In place of, or in addition to, a wound dressing attached to the bottom membrane of the bandage, the wound dressings is is also applied directly to the wound and the bandage placed on top of the wound dressing. Commercially available wound dressings, including for example, calcium alginate, an alginic acid polysaccharide derived from seaweed, available from Dow Hickim Company and from Calgon Company, are suitable for direct application to the wound.

The edges of top membrane 14 and bottom membranes 15 are joined by a leakproof seal 26, to provide a space or chamber 56 between the two membranes.

In the enclosed separator embodiment shown in FIG. 1 the separator 30 is not affixed to the top membrane 14 nor to the bottom membrane 15. Instead, the edges 32, 34 of the top membrane 14 and the bottom membrane 15 extend beyond the separator 30 and the edges 32, 34 of top membrane 14 and bottom membrane 15 are directly sealed. Conventional techniques such as ultra sonic welding, heat sealing, impulse welding, adhesives, or the like, are used to provide a leakproof seal. Heat sealing is preferred. Where the top membrane 14 and bottom membranes 15 are both comprised of Cellguard, the heat sealing provides another advantage because when the two membranes are sealed they turn from opaque to clear.

THE SEPARATOR

Although optional, a separator 30 is preferred. The separator 30 provides rigidity and shape to the bandage 10. The separator 30 separates the top membrane 14 from the bottom membrane 15. The separator 30 should be flexible to permit the bandage 10 to conform to the contours of the wound. Also, the separator 30 should be biocompatible and have a low amount of extractable material. The separator 30 is, optionally, completely enclosed by the envelope 12 as shown in FIG. 1. This is referred to as the "enclosed separator" embodiment. The edges 32, 34 of the top membrane 14 and bottom membrane 15 extend out beyond the separator 30 to permit the top membrane 14 and bottom membrane 15 to be directly joined to provide a leakproof seal. In this embodiment, the separator must be of a suitable size to fit within the envelope 12. The separator 30 is floating free within the envelope 12 as shown in FIG. 1, or attached to the envelope 12 by such conventional means as used to join the top membrane 14 and the bottom membrane 15.

Figure 2:
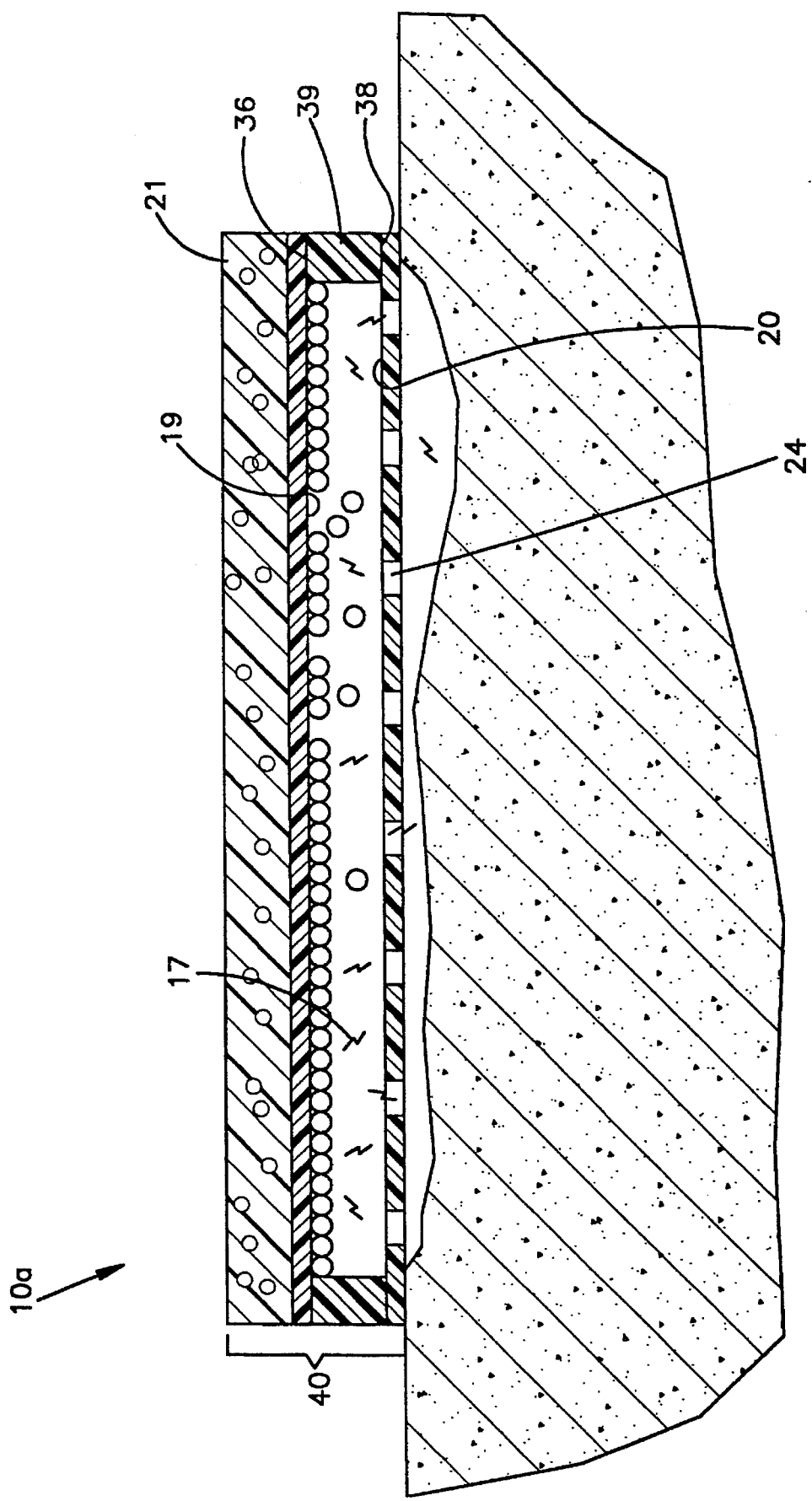
FIG. 2 is a cross-sectional view of the perimeter separator embodiment of the bandage.

In the "perimeter separator" embodiment as shown in FIG. 2, the separator 30 is typically placed between the edges 32, 34 of the top membrane 14 and bottom membrane 15. Both the top side 36 and bottom side 38 of separator 30 are then coated with an adhesive; the top membrane 14 is then affixed to the top side 36 of the separator 30 and the bottom membrane 15 is affixed to the bottom 38 of the separator. Good adhesion between the separator and the membrane has been obtained using medical grade silicone adhesives available under the trade name "Silastic 891-type A" a polysiloxane adhesive from Dow Corning, Midland Mich. If the separator 30 and the membranes 14, 15 are comprised of the same materials, the membranes 14, 15 are typically fused tothe separator 30 by heat sealing. Also, a pressure sensitive medical grade silicone adhesive, available under the trade name "Silastic-type 355" from Dow Corning, is suitable. Medical grade acrylate adhesives are also suitable.

In the perimeter separator embodiment, the separator 30 is placed along the perimeter 40 of the bandage 10 so that it contacts the outside environment. The separator 30 may optionally serve as a point of entry for a syringe needle. For example, where the bandage 10 is to be assembled by injecting the cells 16 into a completely preformed envelope 12, then the needle is inserted through the separator 30, the cells 16 injected, and the needle removed. Thereafter, the separator material seals back around the hole created by the needle.

Thus, where the separator 30 is to serve as a point of entry for a needled the separator material must possess the characteristic of sealing the hole upon removal of the needle; such materials are well known in the art and include, for example, polyethylene, closed cell polyethylene foam, polypropylene, polyurethane, and, preferably, medical grade silicone rubber. Silicone rubber is preferred not only for its ability to close around a needle, but also for its biocompatibility. A suitable medical grade silicone rubber for die stamping to make a separator is available from Variseal Company, in Parkman, Ohio. A suitable closed cell polyethylene foam is sold under the trade name "MED 218A" from Avery in Painsville, Ohio.

Figure 16:
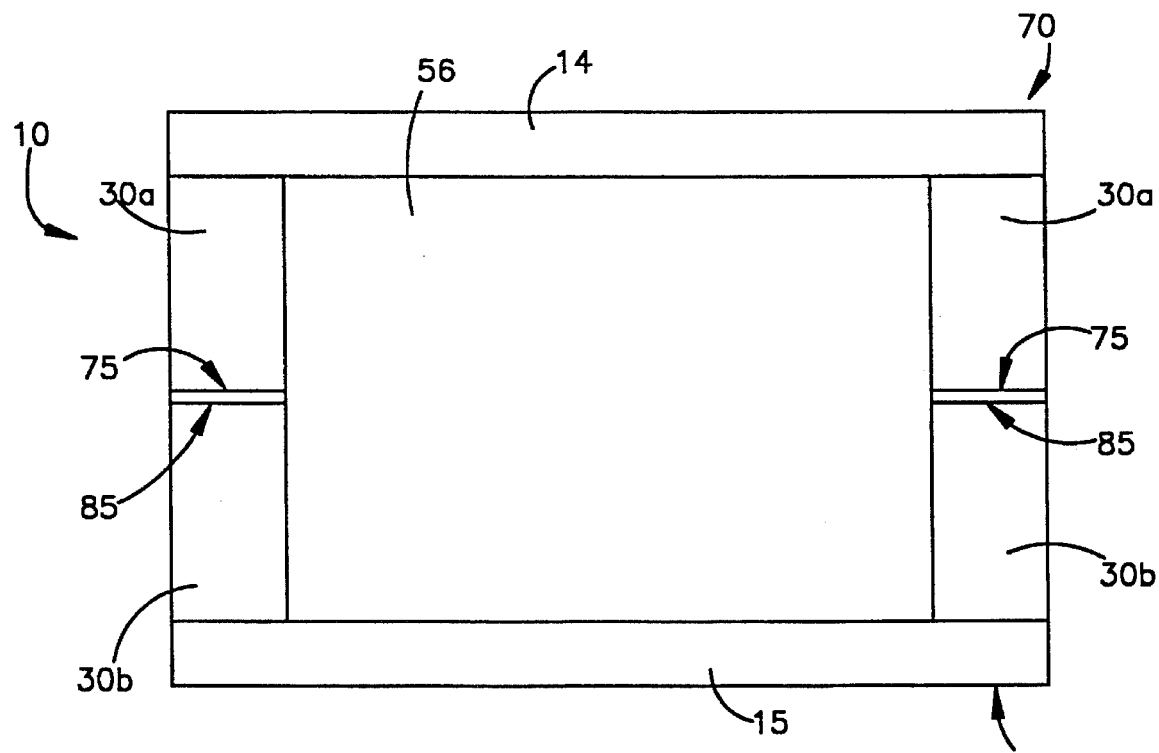
FIG. 16 is a transverse sectional view of another embodiment of the bandage.

In the perimeter separator embodiment, the width of the top surface 36 and bottom surface 38 of the separator 30 must be sufficient to provide adequate surface area for the attachment of the top membrane 14 and the bottom membrane 15. Since the separator 30 size typically increases as the bandage 10 size increases, the width of the top surface 36 and bottom surface 38 of the separator 30 is not fixed. A 4 millimeter top surface 36 and bottom surface 38 is suitable for a bandage 10 of 40–50 mm. in diameter. The height of the separator 30 should be sufficient to provide a perimeter surface 40 through which a syringe needle of about at least 21 gauge may be injected. A separator 30 having about 4 mm. in height is suitable. The top membrane 14 and the separator 30 is optionally formed, such as by molding, into a single continuous structure which are composed of, for example, medical grade silicon, polysulfones or polyethylenes. Another embodiment, shown in FIG. 16, is comprised of top membrane 14, which is preferably a single piece of cast medical grade silicone rubber, having edge 75. Preferably the separator 30 is also comprised of unpolymerized medical grade silicone rubber which is bonded to bottom membrane 15. For example, unpolymerized medical grade silicone rubber which, when polymerized, forms separator 30, is cast into a ring mold with bottom membrane 15, preferably Z-bind, underneath. By applying slight pressure so that the unpolymerized silicone contacts the bottom membrane 15, the medical grade silicone rubber, when polymerized, will be bonded to the bottom membrane 15. The edge 85 of separator 30 is then affixed to the edge 75, preferably, edges 75 and 85 are affixed using silicone rubber glue.

Figure 3:
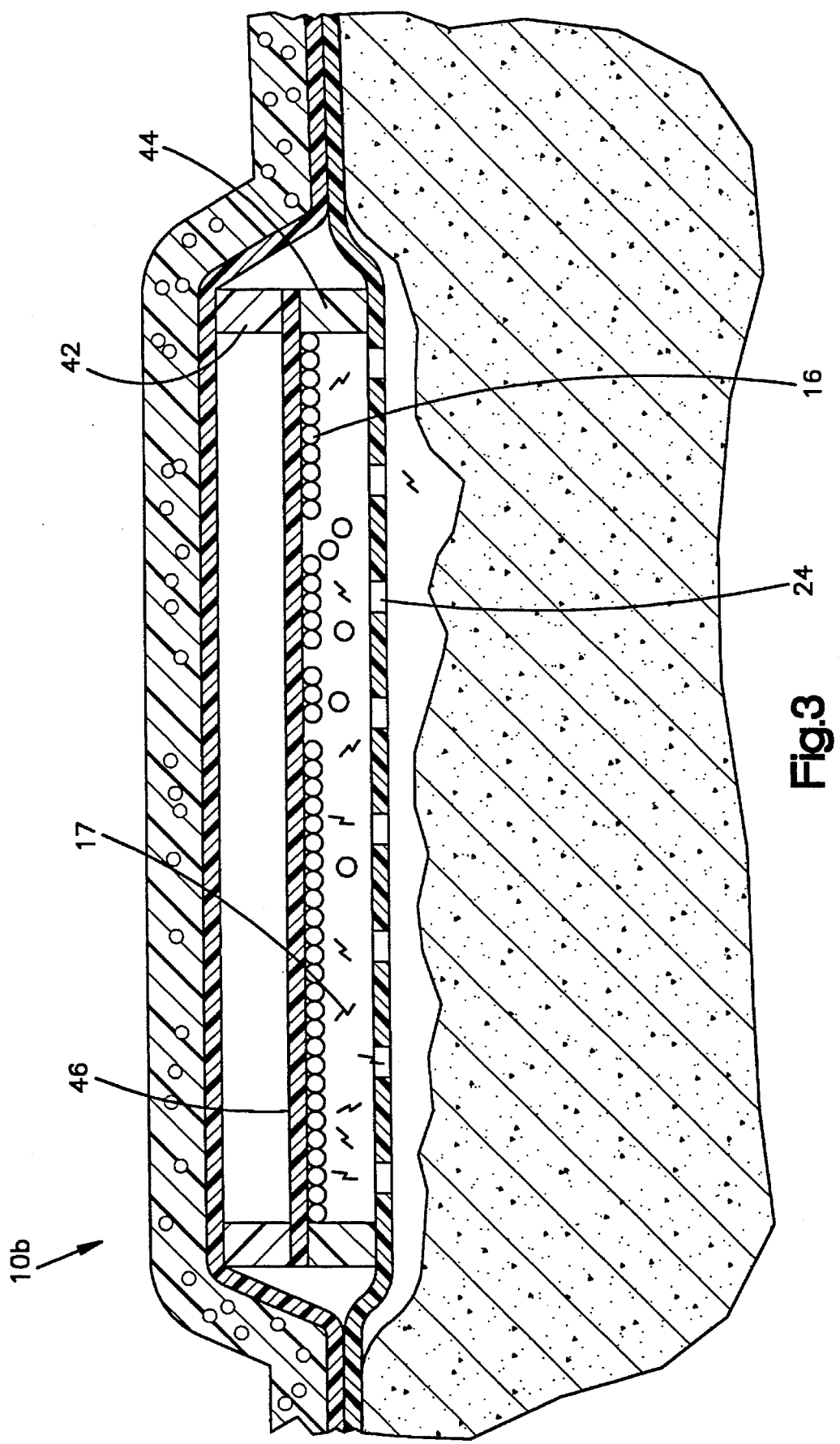
FIG. 3 is a cross-sectional view of an embodiment in which an additional membrane is positioned between separators and enclosed by the bandage.
Figure 4:
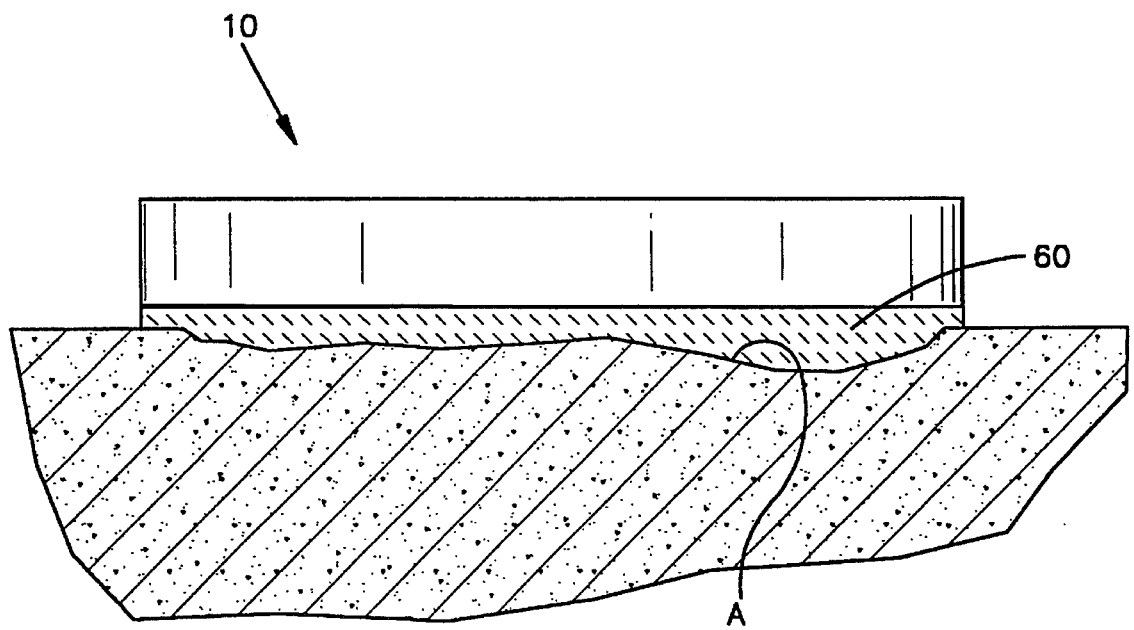
FIG. 4 is a cross-sectional view of the perimeter separator embodiment of the bandage in use with a gel.

In the embodiment shown in FIG. 3, the separator 30 is comprised of two members 42, 44 with a film 46 interposed there between. This embodiment is most useful where the cells are of the anchorage dependent type. The film 46 provides a suitable surface for the cells 11 to attach and grow. Where the cells are anchorage dependent, it is preferred that the film 46 is hydrophilic. Suitable films include those materials which are used as top or bottom membranes, discussed previously. If the film is of a material that is impermeable to the nutrient media, holes are optionally provided in the film 46 for media circulation, or the separator members 42 and 44 are positioned to permit circulation of media around the film. Where a film which provides a suitable surface for anchorage dependent cells to attach and grow is used in a bandage containing anchorage dependant cells, the top membrane 14 and bottom membrane 15 do not have to be of a material suitable for cell attachment and growth.

OTHER FEATURES

Figure 5:
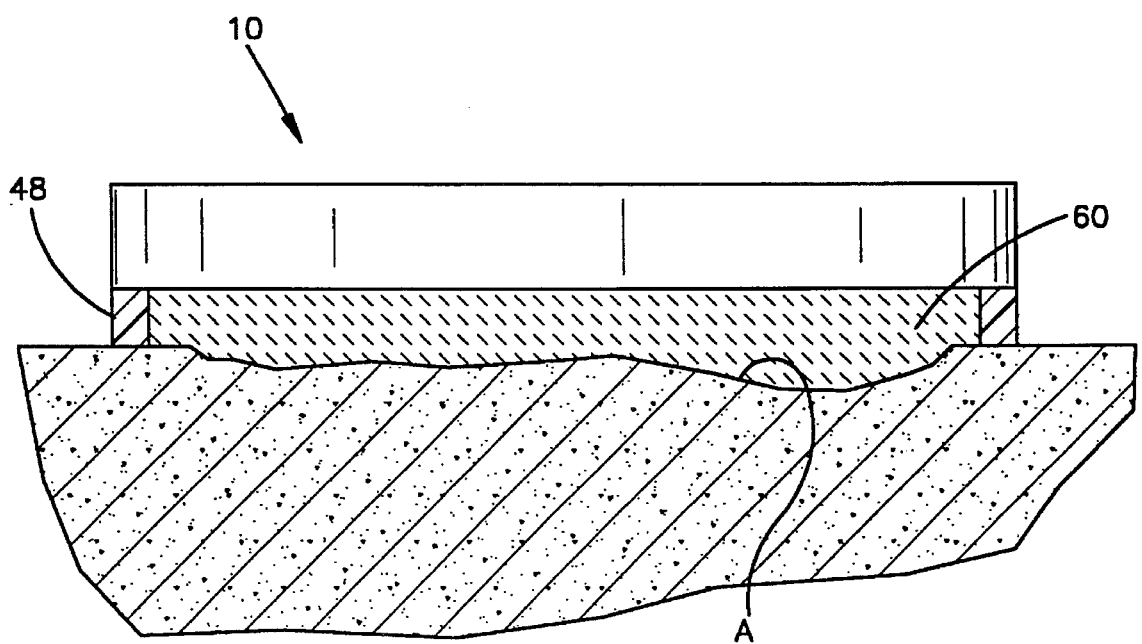
FIG. 5 is a partial cross-sectional view of the bandage with attached separators resting on the wound site, and also showing the use of the gel.

Optionally, as shown in FIG. 5, the bandage 10 has spacer 48 or spacers attached to the bottom side 50 of the bottom membrane 15. The spacers lift bandage off the wound and provide a space between the bottom of the bandage and the wound. The space 52 between the bottom 50 of the bottom membrane 15 and the wound is optionally filled with a wound dressing.

THE CELLS

A variety of natural cells or genetically engineered cell line types may be used. It is preferred that the cells be epithelial or mesenchymal, which is derived from epidermis. Such epithelial or mesenchymal cells are preferred because, when transfected with a growth factor gene or other gene, expression products other than the desired growth factor should be similar to expression products of the cells of the wounded tissue.

The immortality preference is desired from a practical perspective. An immortal cell line facilitates the engineering aspects and maintaining the stock of cells. Good results have been obtained using a squamous cell carcinoma arising from human epidermal keratinocytes, designated "SCC-13" available from Dr. James Rheinwald, Harvard Medical School. Other "SCC" cell lines could also be used such as, for example, SCC-4 American Tissue Type Accession No. CRL1624, SCC-25 American Tissue Type Accession No. CRL-1628 and SCC-9 American Tissue Type Accession No CRL-1629. Other surface epithelial cells may also be used.

The cells may be engineered to produce a variety of growth factors or hormones including, for example, fibroblast growth factor (FGF), epidermal growth factor (EGF), transforming growth factor-alpha (TGF-alpha), transforming growth factor-beta (TGF-beta), platelet derived growth factor (PDGF), insulin, and bovine growth hormone (bGH).

GENETIC ENGINEERING OF THE CELLS

Conventional vectors such as phages and viruses are useful to genetically engineer the cells. However, plasmid vectors which contain no viral oncogene sequences, and no intact viruses, are preferred, to eliminate risk of release of oncogenes or viruses into the patient.

Plasmids useful in this aspect of the invention are synthesized containing the gene for the desired growth factor along with a suitable promotor and terminator signal. The plasmid preferably is constructed to include a marker gene such as a gene conferring drug resistance, for example a gene conferring antibiotic resistance. Good results have been obtained using the neo$^r$ gene which provides resistanae in eukaryotic cells to the neomycin analog designated "G418"

The cells are genetically engineered by transfection with the plasmid. Functional transfected cells are then selected by exposure to the antibiotic. The selected cells are grown and further characterized for the level of production of the desired product. The cells displaying the highest level of growth factor or hormone production are maintained in culture using standard culture techniques.

A portion or aliquot of the cells were removed from the culture for use in the bandage. A viable, engineered cell concentration of from 4,000 cells per cm$^2$ to about 75,000 cells per cm$^2$ is used. A concentration of about 20,000 cells per cm$^2$ is preferred. Approximately $0.5 \times 10^6$ plus or minus about $0.1 \times 10^6$ cells within a bandage having a membrane area of 7 cm$^2$ is used.

The engineered cells may be irradiated prior to the placement of the cells into the bandage. Irradiation renders the cells mitotically inactive and prevents future engineered cell division/proliferation. While the bandage is designed to prevent the escape of any cells from the bandage, in the event of an escape of an engineered cell, such as through an accidental rip or tear in the bandage, the irradiation will prevent the proliferation of the engineered cells within the wound site. Irradiation does not, however, prevent the cells from producing cellular product.

Naturally occurring non-genetically engineered cells may alternatively also be used, particularly those cells producing growth hormones or growth factors.

MEDIA

While any commercially available cell culture media that would sustain the engineered cells 16 for the life of the bandage is suitable, preferred media are comprised of: Dulbeco's Modified Eagle Medium, available from Gibco/BRL, Inc., listed in Catalog 92 ©1991; Ham's F-12 nutrient mixture, available from Gibco, Inc., listed in Catalog 92 ©1991; Keratinocyte Growth Media, available from Sigma Chemical Company; and mixtures thereof. The more preferred medium is the Dulbeco's Modified Eagle Medium and the less preferred medium is the Keratinocyte Growth Media. The most preferred media is a mixture of the Dulbeco's Modified Eagle Medium and the Ham F-12 nutrient mixture in a 3 to 1 ratio.

In addition, the media should contain a buffer to maintain the pH of the media. While many different commercial buffers could be used, Hepes buffer, available from Gibco, is suitable. Other additives include: L-glutamine (100×), 10ml/liter of media; Insulin (5mg/ml), 1ml/liter of media; Hydrocortisone (4ug/ml) ($1 \times 10^{-5}$M), 1ml/liter of media; Gentamicin (1000×), 1ml/liter of media; Penn/Strep (100×), 10ml/liter of media; and, NE-AAs (100×), 10ml/liter of media. Typically, about 10 ml Hepes per liter media is added. Also, if the bandage is to be used on humans, it is preferred that the media does not contain any color indicator to indicate change in pH. In addition, the cell media may be provided with antibiotics such as penicillin and/or streptomycin to reduce bacterial growth.

While the media has been described as a liquid media, the invention encompasses solid and/or gelled media as well. The media may optionally be carried by an gelled material such as Hypolgel positioned in the chamber 56 of the envelope 12.

ASSSEMBLY OF THE BANDAGE

The bandage 10 is assembled in a variety of ways, largely depending on the desired embodiment. In one assembly method for a perimeter separator embodiment in FIG. 2, the inner surface of the perimeter of the top membrane 14 is applied to the top side of an adhesive coated separator 30. With the separator surface up, the cells 16, suspended in media 18, are placed inside the top membrane 14. For the approximately $1 \times 10^6$ cells, 10 milliliters of media are provided. After the cells 16 have attached to the inner surface 17 of the top membrane 14, the edge 34 of the bottom membrane 15 is affixed to the bottom side 38 of the adhesive coated separator 30. Typically, the bandage 10 is then turned with the permeable bottom membrane 15 down and placed in a culture dish. After equilibrating for about 60 minutes, the bandage 10 is then ready for use.

Alternatively, the envelope 12 is assembled as described for the perimeter embodiment, but without placing the cells 16 in the bandage 10 until after the envelope 12 has been completely assembled. After the envelope 12 is completely assembled, the cells 16 which are suspended in media are placed into a syringe, and the syringe needle is inserted through the sidewall of the separator 30. The syringe contents are then injected into the interior space 56 of the bandage 10. The bandage 10 is placed in the incubator to equilibrate before placing the bandage 10 on a patient. The latter method of assembly is suitable if the engineered cells 16 are to be transported to the clinic in a separate container such as a syringe or a vial. The engineered cells 16 could then, after any necessary thawing, be injected into the bandage 10.

In the enclosed separator embodiment shown in FIG. 1, the separator 30, whose diameter or perimeter is at least slightly smaller than the top membrane 14 and the bottom membrane 15, is placed within the top membrane 14. Then an appropriate amount of cells 16 are added. The bottom membrane 15 is placed over top membrane 14 which now contains the cells 16. The edges of the two membranes 14, 15 are joined to provide a leakproof seal.

Modifications may be made to the various methods of assembly. These modifications may arise out of shipping considerations or the shelf life of the engineered cells 16. For example, the engineered cells 16 are sent to a clinic in a sealed frozen vial. After thawing, the desired quantity of engineered cells 16 are removed and injected into the bandage. Alternatively, the engineered cells may be frozen in a syringe, then thawed and injected into the bandage as needed.

APPLICATION OF THE BANDAGE

After the assembly of the bandage 10 and proper equilibration of the genetically engineered cells 16, the bandage 10 may be applied to the wound. Once the bandage 10 is in place, it has a usable life expectancy of up to about 4 to 5 days. At that point, the bandage 10 may be removed or the media 18 in bandage 10 may be replenished to prolong its useful life. The bandage 10 may be replenished by aspirating spent media through a syringe needle inserted through the separator sidewall 39 and injecting fresh media through a syringe needle inserted in the separator sidewall 39 to replace the spent media.

However, as discussed above, the preferred method of treating the wound involves the sequential application of a series of bandages. In the preferred method, a bandage would only be left on about 3 to 4 days, depending on the rate of healing.

Example 1

The bovine growth hormone (bGH) producing bandage.

A bovine growth hormone cellular product was designed to generally demonstrate the functioning of the bandage and specifically to show that: engineered cellular product could be made and secreted by living cells within the bandage; and that the engineered cellular product could pass through the pores of the bandage, into an actual wound site. Since wounded rats are used to demonstrate the diffusion of cellular product into a wound site, it was necessary to have an engineered cellular product such as bGH that can be distinguished from the rats' own cellular products.

To produce an engineered cell that will produce bovine growth hormone, a plasmid designated pNEO-CMV-bGH was obtained from Dr. Fritz Rottman, Department of Microbiology and Molecular Genetics, Case Western Reserve University, Cleveland, OH. This plasmid, which contains the bovine growth hormone with a cytomegalovirus (CMV) promotor and a bovine growth hormone terminator, was synthesized as outlined below.

Construction of pNEO-bGH

Figure 6:
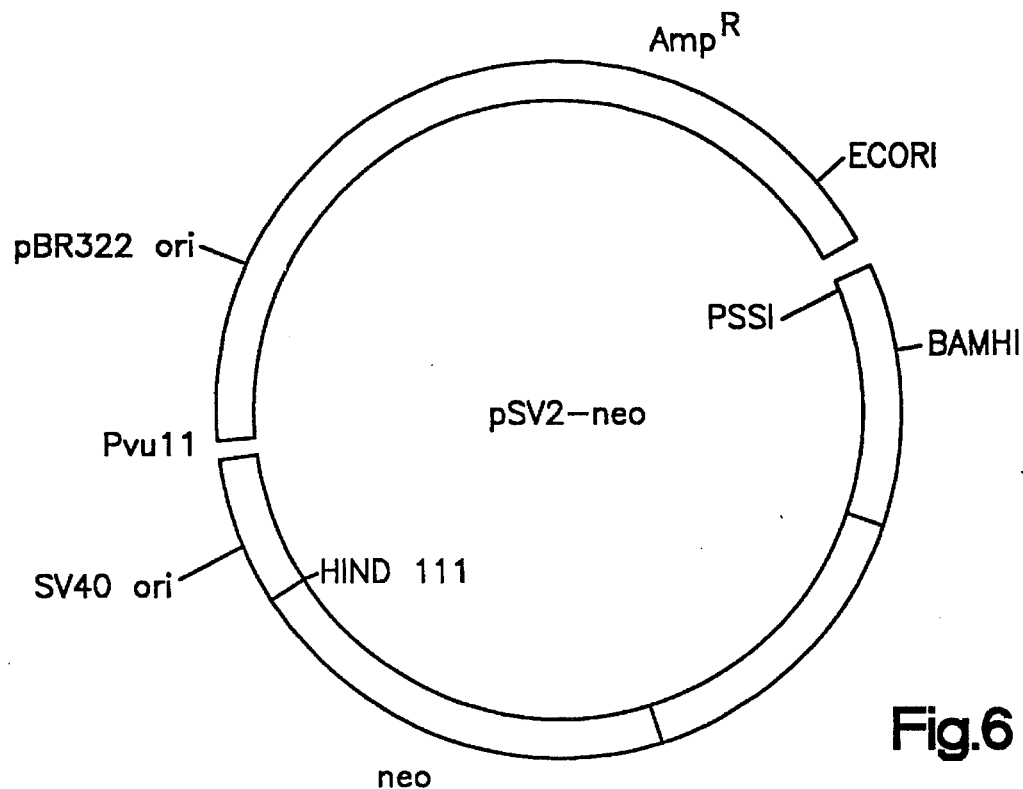
FIG. 6 is a schematic drawing of plasmid $pSV_2NEO$.
Figure 7:
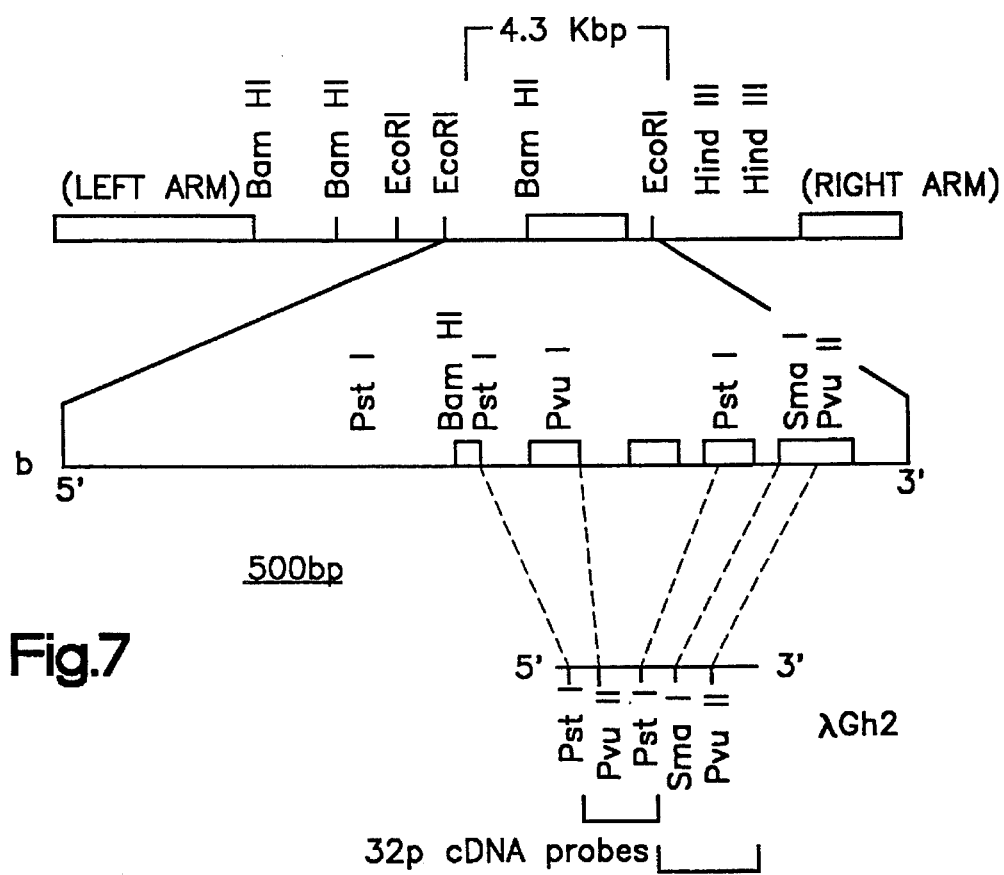
FIG. 7 is a schematic drawing of plasmid $\lambda GH_2$.

Plasmid pSV2NEO, which contains an ampicillin resistance gene, may be obtained from the American Type Culture Collection, Rockville, Md., the Accession No. is 37149. pSV2NEO is shown in FIG. 6. Plasmid pSV2NEO was simultaneously digested with 10 units each of the restriction endonucleases BamHI and EcoRI from New England Biolabs, in Beverly, Mass., in a standard restriction enzyme buffer of 10 mM Tris-HCl, pH 7.2 which contains 100 mMNacl, 10 mMMgCl, 1 mMBeta-mercaptoethanol and 100 μg/ml bovine serum albumin, for about 2 hours at 37° C. The plasmid backbone was isolated by gel electrophoresis on a 1% agarose gel. The approximately 3.5 kilobase band was isolated and precipitated with ethanol.

The method of isolating bovine growth hormone genomic clone λGH2 from a genomic DNA library is disclosed in "Cloning and Nucleotide Sequencing of the Bovine Growth Hormone Gene," Woychik, Camper, Lyons, Horowitz, Goodwin & Rottman, Nucl. Acids Res. 10:7197–7210, 1982. Genomic clone λGH2, containing the complete bGH gene which has approximately 1.8 kilobase pairs, was digested with about 10 units BamHI and about 10 units EcoRI for about 2 hours at 37° C. in standard restriction enzyme buffer. The approximately 1.8 kilobase pair (Kb) BamHI/EcoRI bGH gene fragment was isolated by gel electrophoresis on a 1% agarose gel and precipitated with ethanol.

The approximately 1.8 Kb BamHI/EcoRI bGH gene fragment and BamHI/EcoRI-digested pSV2 NEO were then combined in a 1:1 molar ratio and ligated for 20 hours at 15° C. with about 2 units of T4 DNA ligase from New England Biolabs.

The ligation product was then transfected into E. coli strain NM522 (available from American Type Culture Collection, Accession No. 47000), although any E. coli strain could be used. The transfection was accomplished in a conventional manner by exposing the bacteria to 0.1 molar $CaCl_2$ and removing 100μliters of bacteria grown to an $O.D._{660}$ of 0.6. The bacteria were then incubated with the ligation product for 30 minutes at 4° C., and then warmed to 37° C. for about 2 minutes. This mixture was then transferred to an agar plate containing 50 μg/ml ampicillin, and grown overnight at 37° C. Since the plasmid contains a gene which confers resistance to ampicillin, those E. coli. which took up the plasmid survived in the presence of the ampicillin to form colonies. Thereafter, the colonies were transferred to about 3 mls of growth broth known as "LB-Broth," the components of which are disclosed in "Molecular Cloning: A laboratory Manual," Cold Spring Harbor Press, Cold Spring Harbor, N.Y., Maniatis, Fritsch, Sambrook, (1982), pages 440, and shaken at 37° C. for 6 hours. The bacteria were then grown to confluence.

Figure 8:
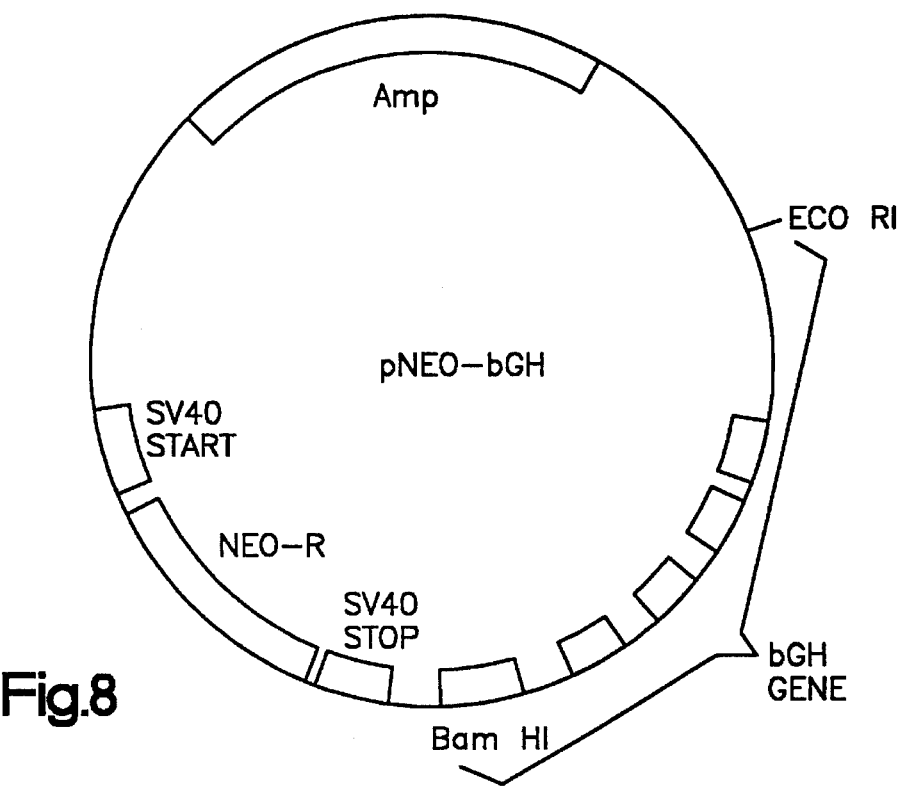
FIG. 8 is a schematic drawing of plasmid pNEO-bGH.

Plasmids were isolated for restriction mapping to verify that the 1.8 Kb BamHI/EcoRI bGH gene fragment was ligated into plasmid pNEO-bGH at the BamHI/EcoRI sites. The plasmids were isolated by removing 1.5 mls of the broth and utilizing the "mini prep" method disclosed in "New Vectors for Rapid Sequencing of DNA Fragments by Chemical Degradation," Eckert Gene Volume 51, 247–254 (1987) The plasmid were then simultaneously digested with BamHI and EcoRI for 2 hours at 37° C. The plasmid fragments were electrophoresed on 1% agarose gel. The presence of the 1.8 Kb bGH gene fragment and the plasmid backbone of about 3.5 Kb confirmed the proper construction of the plasmid. Plasmid pNEO-bGH is depicted by FIG. 8.

Construction of pNEO-CMV-bGH

Plasmid pNEO-bGH was digested with about 10 units of BamHI for about 2 hours at 37° C. in standard restriction buffer and then about 2 units of alkaline phosphatase was added to the mixture and further incubated for about 2 minutes at room temperature. The 5.3 Kb plasmid was then electrophoresed on a 1% agarose gel isolated and precipitated with Ethanol.

In a separate reaction, a 0.75 Kb fragment containing the CMV promoter was isolated from the cytomegalovirus genome by digestion with about 10 units of a restriction endonuclease Sau3A, from New England Biolabs, in a standard restriction buffer at 37° C. for about 2 hours. A CMV promoter from other sources may also be used. The approximately 0.75 Kb CMVpromoter fragment was isolated by electrophoresis on a 1% agarose gel and precipitated with ethanol. The CMV promoter fragment was combined with the previously BamHI digested and dephosphorylated pNEO-bGH fragment, in a 1 to 1 molar ratio and ligated in the presence of about 2 units of T4 DNA ligase for 20 hours at 15° C.

Figure 9:
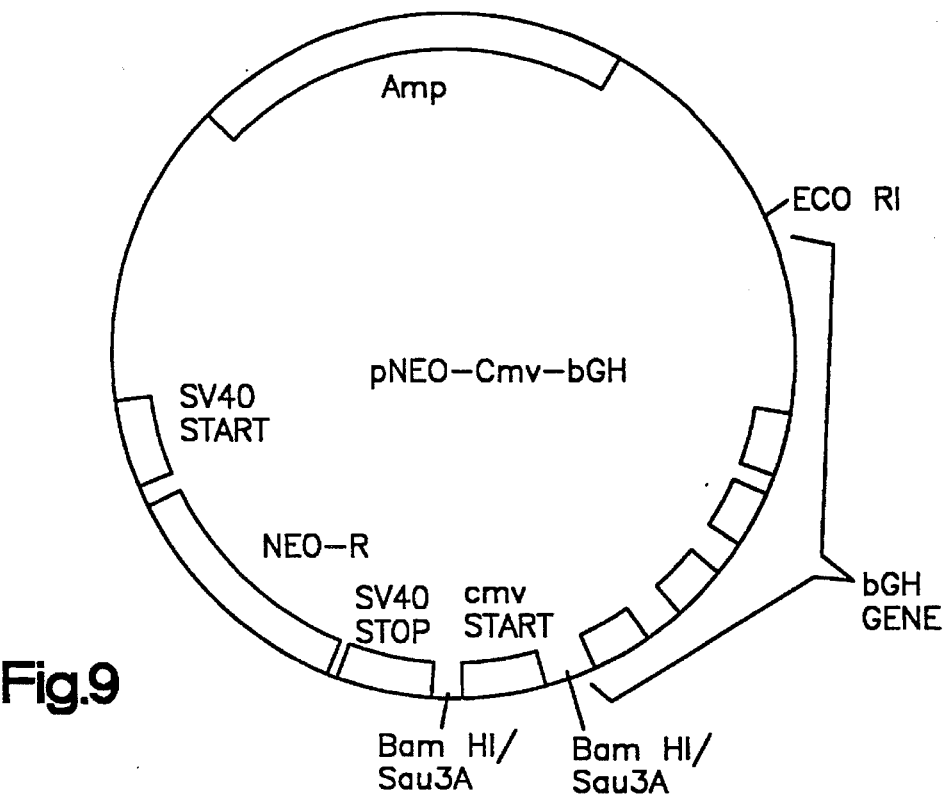
FIG. 9 is a schematic drawing of plasmid pNEO-CMV-bGH.

The ligation product was then transfected as described above into *E. coli* strain NM522 and an ampicillin resistant clone containing the CMV promotor fragment was isolated. This plasmid is designated pNEO-CMV-bGH. To verify that the CMV fragment was ligated into plasmid pNEO-bGH and that the CMV promoter fragment was in the correct orientation to the bGH gene, the plasmids were isolated as described above. The plasmid pNEO-CMV-bGH was simultaneously digested with restriction endonucleases NcoI, and PSTI and the plasmid fragments were electrophoresed on 1% agarose gel. The presence of fragments of about 0.59 Kb and about 0.29 Kb confirmed the presence of the promotor in the correct orientation. As FIG. 9 shows, plasmid pNEO-CMV-bGH contains the CMV promoter upstream of the complete bGH gene so that the CMV promoter regulates transcription of the bGH gene. pNEO-CMV-bGH also contains the separate transcription unit encoding the neomycin phosphotransferase gene under the control of the SV40 promoter and the SV40 transcription terminator.

The plasmid, and hence the cells transfected herewith, contain no viral sequences other than the portion of the CMV promoter, SV40 promoter and the SV40 terminator.

Transfection of the Skin Cells

The pNEO-CMV-bGH plasmid obtained from Dr. Rottman, was used to transfect the SCC13 cells to produce bovine growth hormone producing cell lines for the bandage. SCC13 cells were plated at $2\times10^5$ cells/50 cm$^2$ and allowed to attach overnight. The next day the cells were transfected with 10 μg of the pNEO-CMV-bGH plasmid DNA. Transfection of the cells was accomplished using the established polybrene method as described in "High Frequency Transfection of CHO Cells Using Polybrene," Chaney, Howard, Pollard, Sallustio and Stanley, Somat. Cell Mol. Genet. 12:237–244, 1986. Three days after transfection the cells had grown to confluence. The cells were then harvested and split at a ratio of 1 to 4 into new culture dishes and allowed to attach overnight. Neomycin G418 was then added to the culture medium at a concentration of 200 μg/ml. Fresh medium containing G418 was added to the cultures every 3 days. G418 kills eukaryotic cells. However, cells that have taken up the plasmid that encodes the neomycin phosphotransferase gene are resistant to G418, and survive to form colonies. The colonies were allowed to expand 6 weeks and then characterized for bovine growth hormone production. The detection of growth hormone produced by the genetically engineered cells was accomplished primarily by the well known antibody method of immunoblotting, although immunohistology and immunoprecipitation techniques may also be employed.

Characterization of Growth Hormone Secreting Skin Cells

The potential growth hormone secreting cells were screened for secretion of growth hormone. The cells were grown until confluent in a 10 cm diameter dish (50 cm$^2$) in normal growth media. The media was Dulbecco's Modified Eagle media in a 3 to 1 ratio with Ham's F12 and contained the supplements described above, and 80 ml fetal calf serum per liter. The cells were then shifted to serum-free growth media. After various periods of time (1–24 hours), the medium was collected, concentrated and fractionated on a 12% polyacrylamide gel. The fractionated proteins were blotted to nitrocellulose and incubated with anti-bGH primary antibody followed by secondary incubation with $^{125}$I-labelled protein A, from Amersham Inc. The bands were visualized by exposure on x-ray film (autoradiography).

After exposure on x-ray film, the autoradiographic images were quantitated by laser densitometry.

Significant quantities, that is about 0.1 μg of growth hormone, were released from the cells as early as 1 hour after the beginning of the testing. By 24 hours there was greater than 1.0 μg of bGH in the culture medium. Since one confluent dish of these cells represents approximately $2\times10^6$ cells, the level of hormone production is extremely high. These results confirm the construction of a plasmid, pNEO-CMV-bGH, that produces a high level of hormone.

RELEASE OF ENGINEERED CELLULAR PRODUCT FROM THE ASSEMBLED BANDAGE

The bandage was assembled according to the enclosed or perimeter gasket embodiment. Thereafter the bandage's efficiency was determined by measuring the amount of engineered cellular product secreted into the media surrounding the cells and the media outside of the bandage. The bandage's efficiency was also determined by placing the bandage onto rat wounds.

The engineered cells were seeded into the bandage and allowed to attach to the inside of the inside surface of the top membrane to form the bandage shown in FIG. 2. The inside of the bandage contained serum-free growth medium to maintain the engineered cells. The bandage was a 7 cm diameter circle that contained $1\times10^6$ cells.

The daily level of growth hormone in the medium inside and the medium outside of the bandage was measured for a period of 10 days. The results indicate that the cells remain viable in the minimal media for 10 days and that they release growth hormone into the internal and external medium at a steady rate of about 1.0 μg/$1\times10^6$cells per day. The bottom membrane did not impede the release of the growth factor from the bandage or the cells.

Figure 15:
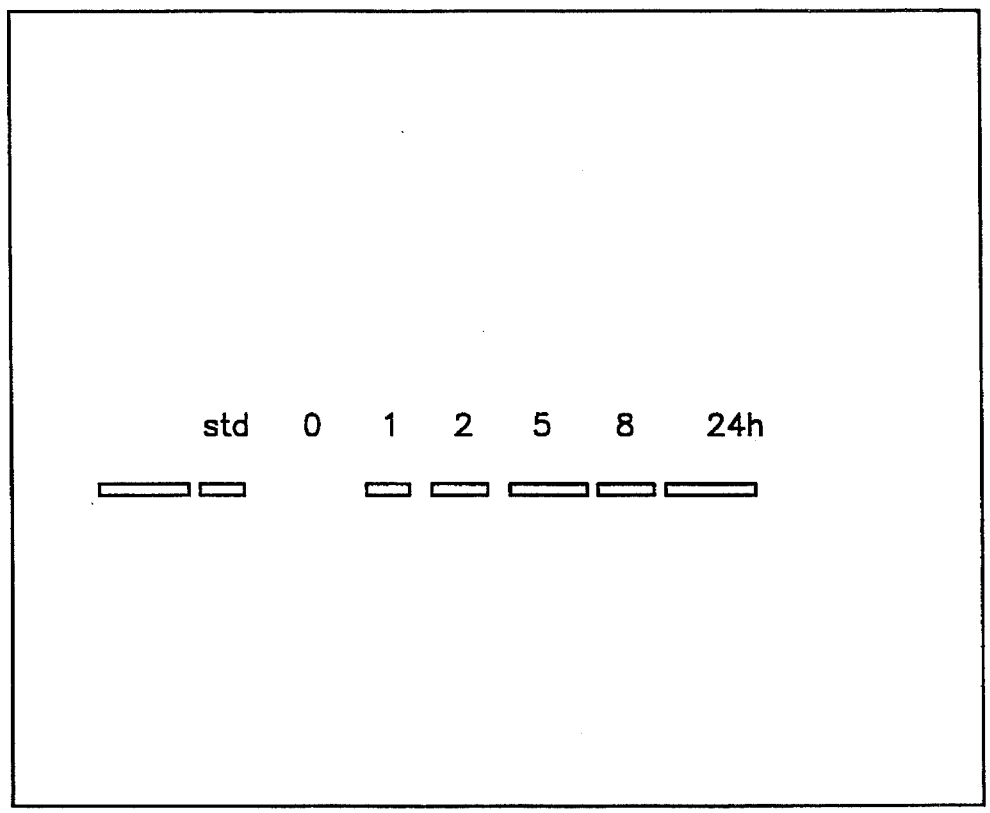
FIG. 15 is an autoradiograph of bovine growth hormone released from cells located within the bandage.

For detection of growth factor released from the bandage into the medium, the engineered cells were shifted to serum-free defined medium and incubated for 1 hour to 10 days. At various times the medium was collected and concentrated/desalted using an Amicon centricon-10 filter. This filter retains molecules with molecular weights greater than 1000 daltons. The retained proteins were then washed with Tris-HCl, at pH 7.0 containing 0.1 mM EDTA, dissolved in electrophoresis sample buffer and electrophoresed on a 10% acrylamide gel. Immunological detection of the growth factor was both by immunoblotting with a bGH specific antibody and by a radioactively labelled $^{125}$I protein A from Amersham, Inc. FIG. 15 is an autoradiograph showing the release of bGH from the bandage over 24 hours time. The "std" is a standard containing 0.5 μg of bGH.

RAT WOUND APPLICATION

A circular ring made from medical grade silicone rubber was glued to a shaven skin of anesthetized rats. The walls of the ring were 0.4 cm thick and 0.4 cm high. The center of the ring had an opening the size of a quarter and is the site of the wounding. The purpose of the ring is two fold. Firsts, it provides a chamber where the wound can be prepared and monitored, and second, it prevents the wound from contracting.

The wound was produced by heating a circular, flat iron piece to 70° C. in a hot water bath and placing it on the surface of the skin for 30 seconds. The iron has a diameter slightly less than the wound chamber diameter so that the iron could be easily placed within the chamber. This device and method produced a uniform burn on the surface of the rat skin. The extent of the burn can be controlled by varying the time of exposure or by performing multiple exposures.

A gelatin layer was placed on the rat wound. A bandage having a diameter smaller than the chamber diameter, was placed atop the gelatin layer and covered the wound. Finally, a transparent wound chamber cover made of a biocompatible film with adhesive edges that seals the wound chamber was placed over the chamber. The closed wound chamber was then wrapped with an elastic band that was held in place by stitches to prevent the rat from removing or damaging the bandage.

The engineered cellular product produced by the biological bandage was determined by measuring the amount of the engineered cellular product present in the fluid that collected within the wound chamber.

The amount of engineered cellular product present in the wound area was approximately 50 nanograms. More or less engineered cellular product may be delivered by increasing or decreasing the concentration of the engineered cells present within the bandage.

Example 2

The Human Epidermal Growth Factor Producing Bandage

Figure 10:
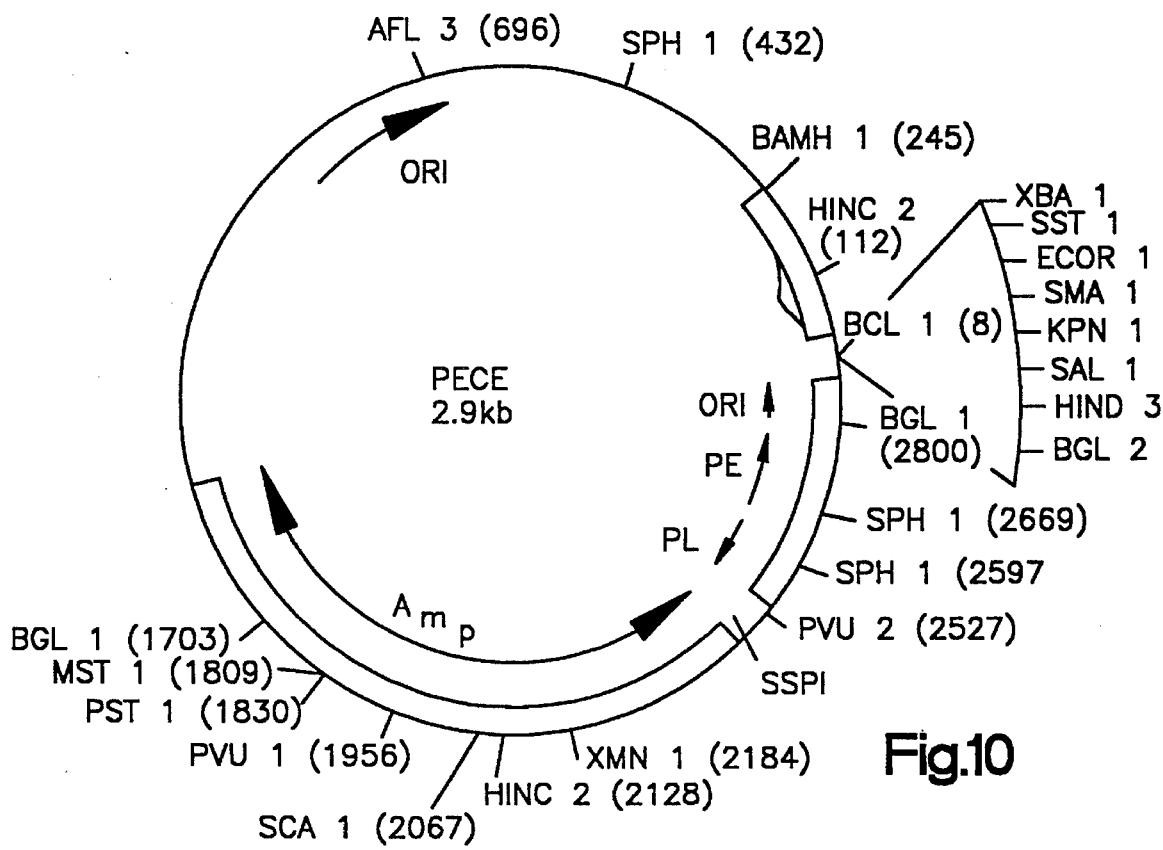
FIG. 10 is a schematic drawing of plasmid pECE.

A plasmid containing the human epidermal growth factor gene coding sequence and a neomycin resistance gene was prepared in several steps. A plasmid "pECE" was obtained from Dr. Rutter in the University of California, San Francisco, synthesized according to the method disclosed in "Replacement of insulin receptor tyrosine residues 1162 and 1163 compromises insulin-stimulated kinase activity and uptake of 2deoxyglucose," Ellis L., Clause E, Morgan D. 1O., Edery M., Roth R. A., Rutter W. Y. Cell: 45:721–732(1986). Plasmid pECE is shown in FIG. 10.

Next, the pECE plasmid was cleaved or digested at the SalI site which lies between an SV40 promotor and an SV40 terminator. The digestion was accomplished using a SalI restriction endonuclease from New England Biolabs Company and was carried out according to the methods disclosed in "Molecular Cloning: A Laboratory Manual," Maniatis, Fritsch and Sambrook, Cold Spring Harbor Press, Cold Spring Harbor, N.Y., pp. 104, 452 (1982) for 2 hours at 37° C. in the standard restriction enzyme buffer. The resulting SalI ends were then dephosphorylated by incubation for 3 minutes at room temperature with 2 units of calf alkaline phosphatase available from New England Biolabs. Then the SalI-digested, dephosphorylated, plasmid was purified by electrophoresis on a 1% low melting temperature agarose gel. The approximately 2.9 Kb band, which contains the SalI digested and phosphatase treated pECE plasmid, was isolated from the gel and precipitated with ethanol.

Preparation of EGF Coding Sequence

Figure 11:
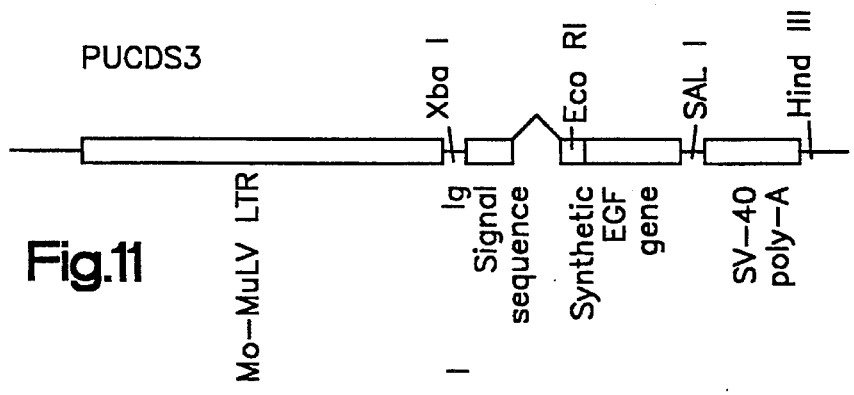
FIG. 11 is a schematic drawing of plasmid pUCDS3.

As FIG. 11 shows, plasmid pUCDS3 contains an Ig signal sequence which encodes for a mouse immunoglobulin heavy chain signal peptide fused to the human EGF coding sequence. Plasmid pUCDS3 was obtained from Dr. Kung, Department of Microbiology and Molecular Genetics, Case Western Reserve University, Cleveland, OH. The production of this plasmid is disclosed in "Construction of a Novel Oncogene Based on Synthetic Sequences Encoding Epidermal Growth Factor" by Stern, Hare, Cecchini and Weinberg, Science 235:321–324, 1987. The plasmid pUCDS3 was first digested with 10 units of the restriction endonuclease XbaI from New England Biolabs for 2 hours at 37° C. and dephosphorylated with 2 units of alkaline phosphatase for 3 minutes and then purified by gel electrophoresis on a 1% agarose gel. The XbaI digested plasmid containing about 3.0 Kb was then isolated.

An oligonucleotide was constructed using a commercially available DNA synthesizer available from Applied Biosystems, Inc., Hayward, Calif., having a double stranded sequence with an internal SalI restriction site flanked by XbaI cohesive ends as follows:

```
5'-CTAGAGTCGACT-3'                SEQ ID NO.: 1
3'-    TCAGCTGAGATC-5'
   XbaI . . . . . . . XbaI
        Sal I
```

Figure 12:
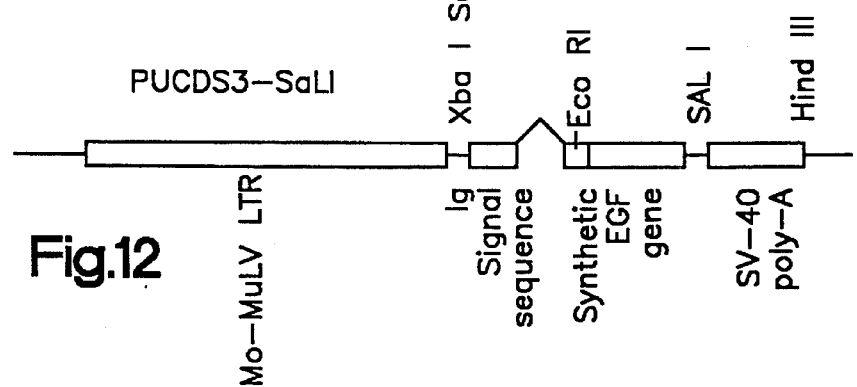
FIG. 12 is a schematic drawing of plasmid pUCDS3-SALI.

The oligonucleotides were kinased on the 5' ends using polynucleotide kinase available from New England Biolabs, and then annealed by incubating in 100 mM Tris-HCl having a pH of 7 and containing 100 mM $MgCl_2$ for 2 hours at 25° C. These steps were performed by standard methods as disclosed by Maniatis at pp. 122–126 and pg. 242. The annealed oligonucleotides were then mixed in a 1:1 molar ratio with XbaI digested pUCDS3 and ligated with 2 units of T4 DNA ligase from New England Biolabs, for 15 hours at 15° C. The ligation product was then transfected into E. coli strain NM522, although any E. coli strain would be satisfactory, and ampicillin resistant colonies were selected. A clone was isolated that contained a plasmid wherein a new SalI site was inserted at the XbaI site. This plasmid is designated "pUCDS3-SalI" and is depicted by FIG. 12. It contains the Ig signal sequence-human EGF fusion gene cloned between two SalI sites.

Transfer of EGF Coding Sequence to SalI-Digested and Phosphatased pECE

Figure 13:
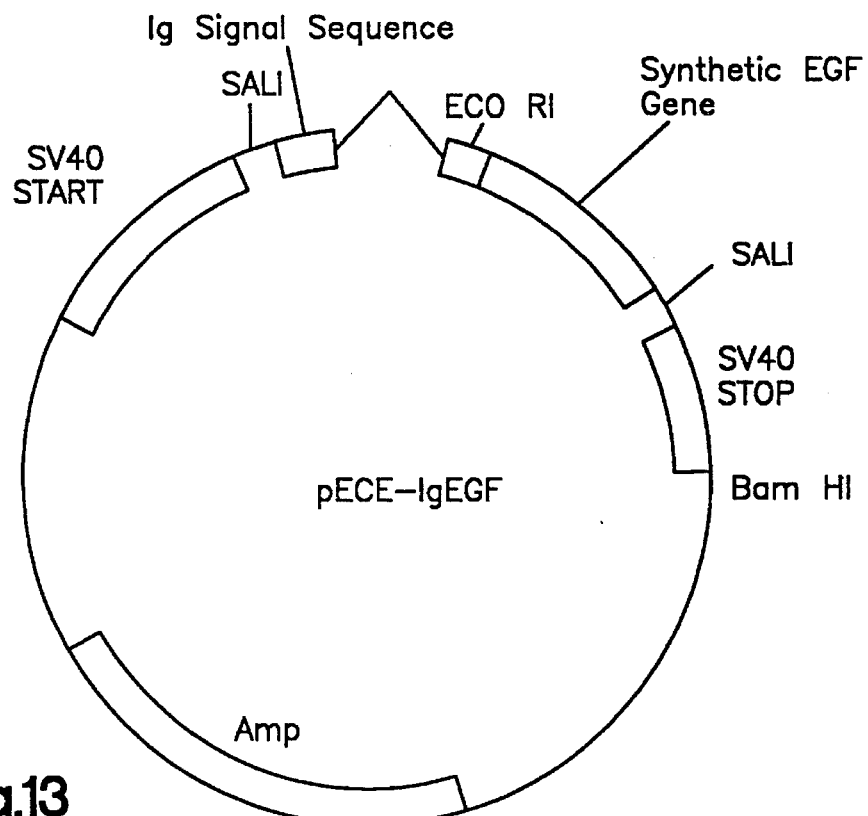
FIG. 13 is a schematic drawing of plasmid pECE-IgEGF.

The plasmid pUCDS3-SalI was digested with SalI for 2 hours at 37° C. The insert that contains the Ig signal sequence-human EGF fusion gene contains approximately 0.5 Kb; it was purified by electrophoresis on a 1% low melting temperature agarose gel, and the approximately 0.5 Kb band was isolated and precipitated with ethanol. This insert was then mixed in a 1:1 molar ratio with the SalI-digested and phosphatase treated pECE and ligated with 2 units of T4 DNA ligase for 15 hours at 15° C. The ligation mixture was then transfected into E. coli strain NM522 and colonies were selected using ampicillin. A clone was isolated that contains the Ig signal-human EGF sequence cloned at the SalI site in the correct orientation for expression from the SV40 promoter present in pECE. This plasmid, pECE-IgEGF, is depicted by FIG. 13.

Transfer of the Neomycin phosphotransferase Gene to pECE-IgEGF

The plasmid pECE-IgEGF was digested with BamHI under standard conditions for 2 hours at 37° C. and then dephosphorylated under standard conditions of 2 units alkaline phosphatase at room temperature for 3 minutes. This plasmid was then ligated in a 1:1 molar ratio with a BamHI cassette containing the neomycin phosphotransferase gene under the control of the Rous sarcoma virus (RSV) promoter and SV40 terminator. The construction of this cassette called (NEO) is described in "Stable expression of transfected human involucrin gene in various cell types; evidence for in situ cross-linking by type I and type II transglutaminase Rorke and Eckert, J. Invest. Dermatol. 97:543–548, 1991. The ligation was performed in ligation buffer using 2 units of T4 DNA ligase for 15 hours at 15° C. under standard conditions.

Figure 14:
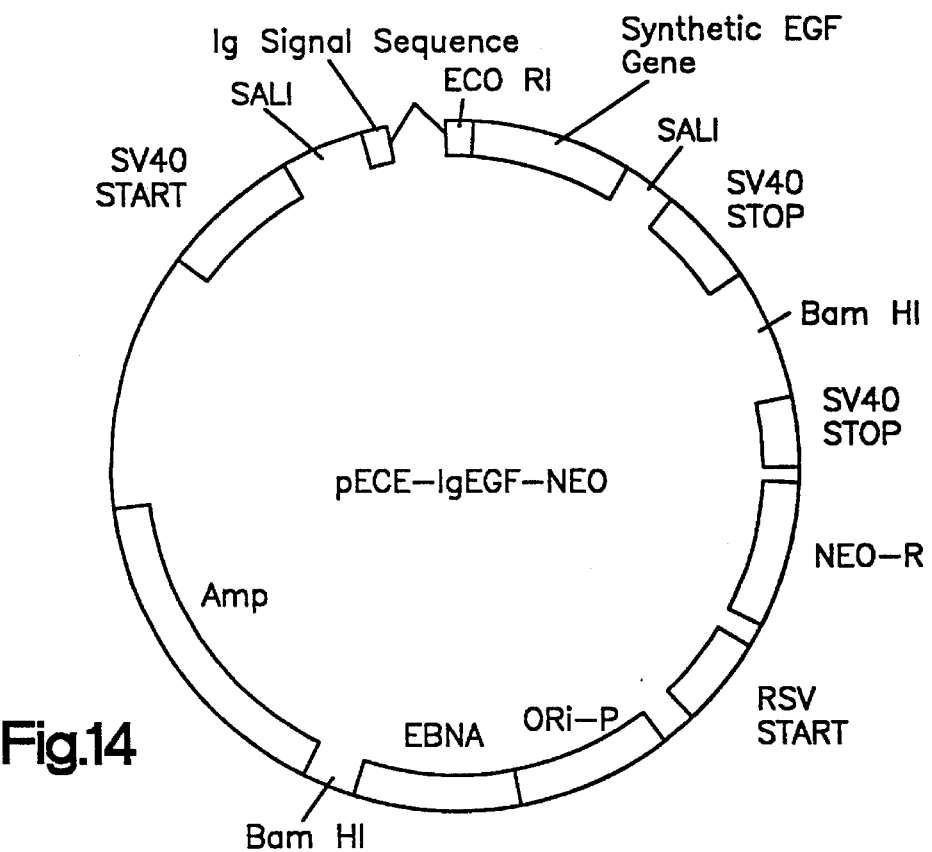
FIG. 14 is a schematic drawing of plasmid pECE-IgEGF-NEO.

The ligation product was then transfected into *E. coli* strain NM522 and ampicillin resistant colonies were selected. To verify that the BamHI cassette ligated into the pECE-IgEGF fragment, a specific clone was purified, restriction digested with BamHI and electrophoresed on 1% agarose gel. The presence of pECE-IgEGF fragment of about 3.2 Kb and the neomycin phosphotransferase gene-containing cassette (NEO) of about 9.0 Kb confirmed the ligation. The resulting plasmid was designated pECE-Ig-EGF-NEO, as shown in FIG. 14.

Transfection of SCC-13 Cells with pECE-IgEGF-NEO

The plasmid pECE-Ig EGF-NEO was then used to transfect SCC-13 cells to produce a human EGF-producing line of skin cells by methods identical to those described above for the production of SCC-13bGH cells. Neomycin resistant clones were selected with 200 µg/ml neomycin G418. The resulting clones were characterized for production and secretion of EGF into the culture medium.

Specifically, a radioimmunoassay kit containing antibody to human epidermal growth factor, available from Biomedical Technology, Inc., Stoughm, Mass., was used to determine the amount of human growth factor present in the media. Approximately 94 pg were secreted by $10^6$ cells after 24 hours.

While in the preceding examples specific viral promotors constituting high level promotions have been used as promotors for a gene that expresses the desired cellular product, such as a growth hormone factor, it should also be understood that other viral promotors such as a CMV promotor, Rous Sarcoma (RSV), and Moloney Murine Leukemia promotor may be used. Inducible promotors may also be used such as, for example, heavy metal ion inducible promotors such as, for example a metalo-thionine promotor or promotors that are responsive to vitamins or hormones such as the retinoic acid inducible promotors. Constitutively active promotors isolated from cellular genes such as, for example, actin may also be used.

Similarly, a wide variety of terminators may also be used, such as, for example, a cellular gene terminator such as bovine growth hormone terminator or actin gene terminator, or a viral terminator, such as the SV40 terminator. In addition, terminators or promotors made in whole or in part by artificially constructed DNA sequences may be used.

It should also be understood that in addition to the neomycin gene marker utilized in this invention, other markers, including for example, puromycin or hygromycin may be used. The gene markers may be used with different promotors and/or terminators than used in the examples. Suitable promotors and terminators include, for example, those terminators and promotors identified in the preceding paragraph.

While the bandage has been described as a means of applying an engineered cellular product such as a growth factor to a wound, the bandage may comprise genetically engineered cells which produce other molecules such as hormones or antibiotics. Also, the bandage may be used to supply such other molecules which may be useful for treating wounds, or to transdermally supply such molecules to the patient through non-wounded tissue for systematic treatment of disease and injury.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 12 base pairs
( B ) TYPE: nucleic acid
( C ) STRANDEDNESS: both
( D ) TOPOLOGY: linear ( x i ) SEQUENCE DESCRIPTION: SEQ ID NO:1:

C T A G A G T C G A   C T                                                         1 2

What we claim is:

1. A kit for forming a bandage, containing cells that secrete a wound healing factor comprising:
   a. a container containing cells that secrete a wound healing factor; and
   b. a bandage comprising:
      i. a first membrane, being gas permeable and fluid impermeable, and
      ii. a second membrane, being permeable to the wound healing factor, said first and second membranes each having a perimeter, and being joined at the perimeter so as to define a chamber for receiving said cells.

2. The bandage kit as defined in claim 1, wherein said bandage further comprises a wound dressing disposed on the bottom of said second membrane.

3. The bandage kit as defined by claim 1 wherein said bandage further comprises a separator disposed between said first and second membrane.

4. A bandage kit as defined in claim 2 or 3 wherein said bandage further comprises a spacer for spacing said bandage from a wound.

5. A bandage kit as defined in claim 2 or 3 in which said bandage further comprises cell culture medium disposed in said chamber.

6. A bandage kit as defined in claim 3 wherein said separator is positioned adjacent to the connection of said first and second membranes.

7. A bandage kit as defined in claim 3, wherein the separator is positioned within said chamber adjacent to said connection of the perimeters of said first and second membranes.

8. A bandage kit as defined in claim 3, wherein said separator is joined to each of said first and second membranes.

9. A bandage kit as defined in claim 3 in which the perimeters of said first and second membranes of said bandage are connected by joining the perimeter of said first membrane to the rod of the separator and by joining the perimeter of the second membrane to the bottom of the separator.

10. A bandage kit as defined in claim 9 in which said second membrane comprises polysulfone and the first membrane is formed of silicone rubber.

11. A bandage kit as defined in claim 1 in which said first membrane comprises polyethylene or polypropylene.

12. A bandage kit as defined in claim 1 in which said first membrane comprises polysulfone.

13. A bandage kit as defined in claim 1 in which said second membrane comprises a non-woven polyethylene or polypropylene fiber.

14. A bandage kit as defined in claim 1 in which said second membrane comprises polysulfone.

15. A bandage kit as defined in claim 3 wherein said bandage further comprises two separator members and film extending across said chamber and bonded to said separator members, wherein said film has a hydrophilic surface to facilitate the attachment of cells.

16. A bandage containing cells that secrete wound healing factors, comprising:
   a. an envelope, comprising a gas permeable and fluid impermeable top membrane and a bottom membrane permeable to the wound healing factor, and a chamber therebetween, wherein the top membrane is interconnected to the bottom membrane to provide a leakproof seal;
   b. cells that secrete a wound healing factor, said cells located within said chamber;
   c. media, for substaining said cells, disposed within said chamber, and surrounding said cells; and
   d. a wound dressing disposed on the bottom side of said bottom membrane.

17. The bandage of claim 16, further comprising a spacer for spacing said bandage from a wound.

18. The bandage of claim 16, further comprising a layer of flexible material on top of the top membrane for providing support and protection to the bandage.

19. A bandage for containing cells that secrete wound healing factors comprising
   a. an envelope, comprising:
      i. a gas permeable and fluid impermemable top membrane and
      ii. a bottom membrane permeable to the wound healing factor, and a chamber therebetween, wherein each of said membranes has a perimeter and wherein the perimeter of said top membrane is interconnected to the perimeter of said bottom membrane to provide a leakproof seal;
      iii. a separator, interposed between said perimeter of said first membrane and said perimeter of said second membrane;
   b. cells that secrete a wound healing factor, said cells located within said chamber, and,
   c. media, for sustaining said cells, disposed within said chamber, and surrounding said cells.

20. The bandage of claim 19, further comprising a wound dressing disposed on the bottom of said bottom membrane.

21. The bandage as defined in claim, 16 or 19 for producing human epidermal growth factor, wherein said cells contain a plasmid comprising:
   an epidermal growth factor gene sequence comprising the following elements in the 5' to 3' direction said elements being operably linked:
      (1) promotor;
      (2) Ig leader sequence;
      (3) human epidermal growth factor gene; and,
      (4) terminator.

22. The bandage as defined in claim 21, wherein the plasmid further comprises two antibiotic resistance gene sequences comprising: the following elements in the 5' to 3' direction, said elements being operably linked:
   (1) a promoter;
   (2) an antibiotic resistance gene; and
   (3) a terminator.

23. The bandage as defined in claim 20, wherein the cells are SCC-13 cells.

24. The bandage as defined in claim 20 wherein the cells additionally contain a plasmid comprising a gene operably linked to a promoter wherein said gene is selected from the group consisting of human PDGF, human EGF, human TGF, and combinations thereof.

25. The bandage as defined in claim 20 wherein the cells contain a plasmid comprising the following elements in the 5' to 3' direction said elements being operably linked:
   (1) a promoter selected from the group consisting of the Moloney murine leukemia virus LTR promoter and the SV40 promotor,
   (2) an Ig leader sequence,
   (3) the human epidermal growth factor gene, and
   (4) the SV40 terminator.

26. The bandage as defined in claim 20 wherein the cells are epithelial cells transfected with a plasmid comprising a gene operably linked to a promotor wherein said gene is selected from the group consisting of human PDGF, human EGF, human TGF, bovine GH, and combinations thereof.

27. The bandage of claim 19, further comprising a spacer for spacing said bandage from a wound.

28. The bandage of claim 19, further comprising a layer of flexible material on top of the top membrane for providing support and protection to the bandage.

29. A method for treating a wound which comprises applying to said wound a bandage as defined by claim 19.

30. A method for treating a wound as defined in claim 29 further comprising the step of applying a wound dressing between said wound and said bandage.

31. A method for treating a wound which comprises the sequential application to said wound of a plurality of bandages as defined in claim 19, wherein at least one of said bandages produce a wound healing factor that differs from the wound healing factor produced by at least one other bandage.

* * * * *